United States Patent [19]

Richtzenhain et al.

[11] 4,057,552
[45] Nov. 8, 1977

[54] PRODUCTION OF CYANOPYRIDINES FROM PIPERIDINES

[75] Inventors: Hermann Richtzenhain, Much-Schwellenbach, Germany; Paul Janssen, deceased, late of Bensberg-Refrath, Germany, by Almuth Janssen, heir

[73] Assignee: The Lummus Company, Bloomfield, N.J.

[21] Appl. No.: 701,694

[22] Filed: July 1, 1976

[51] Int. Cl.[2] .......................... C07D 213/57
[52] U.S. Cl. .................... 260/294.9; 260/290 R
[58] Field of Search .................. 260/294.9, 290 R

[56] References Cited

U.S. PATENT DOCUMENTS

| | | | |
|---|---|---|---|
| 2,592,123 | 4/1952 | Denton et al. | 260/294.9 |
| 3,544,617 | 12/1970 | Oga et al. | 260/294.9 |
| 3,555,021 | 1/1971 | Beutel et al. | 260/250 BN |
| 3,925,447 | 12/1975 | Gelbein | 252/464 |

*Primary Examiner*—Alan L. Rotman
*Attorney, Agent, or Firm*—Marn & Jangarathis

[57] ABSTRACT

Nicotinonitrile is produced from a piperidine having an alkyl substituent in the three position by contact with ammonia, in the absence of molecular oxygen, and in the presence of oxidized vanadia supported on a porous support, containing from 25% to 75%, by weight, of the vanadia, the vanadia having been placed in molten form substantially entirely within the pores of the support, with the support having a surface area greater than 50 m$^2$/gm and a porosity greater than 0.4 cc/gm, with the support being either gamma-alumina or silica-alumina.

6 Claims, 1 Drawing Figure

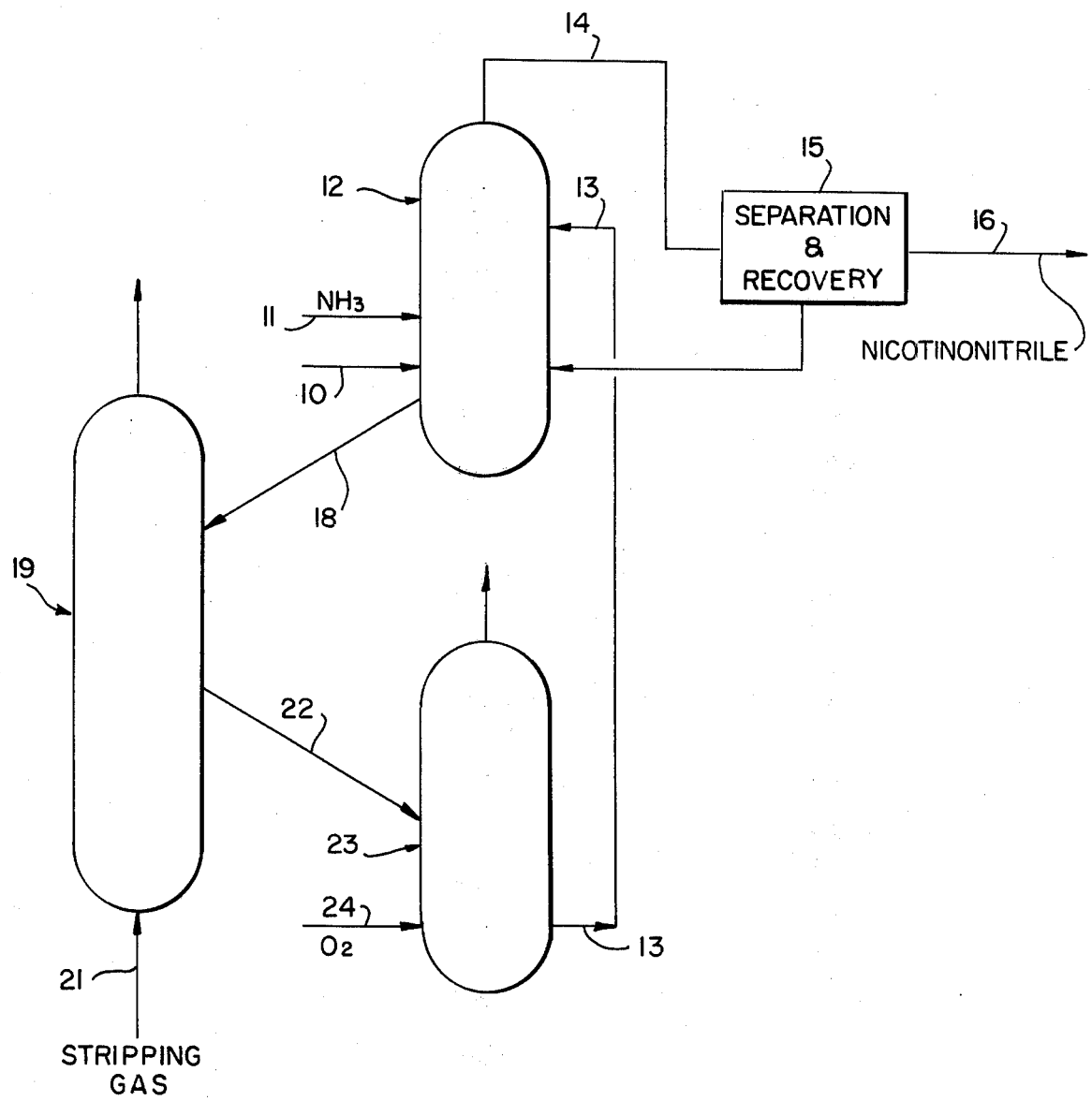

PRODUCTION OF CYANOPYRIDINES FROM PIPERIDINES

This invention relates to the production of cyanopyridines, and more particularly, to a new and improved process for producing nicotinonitrile from a piperidine.

U.S. Pat. No. 3,555,021 discloses a process for the production of a cyanopyridine from an alkyl substituted piperidine by reaction with ammonia and oxygen in the presence of a catalyst of vanadia or molybdena chemically combined with cobalt, vanadium or molybdenum. The patent further discloses that attempts to use vanadium pentoxide for conversion of alkyl substituted heterocyclic compounds resulted in cleavage of the alkyl substituents.

In accordance with the present invention, there is provided a process for converting an alkyl piperidine to the corresponding cyano-substituted pyridine by reaction with ammonia, in the absence of molecular oxygen, and in the presence of oxidized vanadia supported on a porous support in an amount from about 25% to about 75%, by weight, with the vanadia having been placed in molten form substantially entirely within the pores of the support. The support has a surface area greater than about 50 $m_2/gm$ and a porosity greater than about 0.4 cc/gm and is either gamma-alumina or silica-alumina.

The starting materials employed in the present invention are alkyl substituted piperidines. The substituted piperidines are generally alkyl substituted piperidines having alkyl groups containing from 1 to 5 carbon atoms, with the ring being substituted with one or more such alkyl groups. As representative examples of such starting materials, there may be mentioned: 2-, 3-, and 4-methyl piperidine; 2-, 3-, and 4-ethyl piperidine; 2,3-dimethyl piperidine; 2-methyl-5-ethyl piperidine; 2,4-dimethyl piperidine; 2,5-dimethyl piperidine; and the like.

The present invention is particularly applicable to the production of nicotinonitrile from an alkyl piperidine having at least one alkyl group, with the at least one alkyl group being substituted in the three position. More particularly, the starting material for producing a nicotinonitrile is a 3-alkyl piperidine, 2,3-dialkyl piperidine or a 2,5-dialkyl piperidine.

The supported vanadia catalyst, as hereinabove described, is oxidized vanadia; namely, vanadium pentoxide, which is present in an amount from about 25% to about 75%, preferably from about 30% to about 60%, all by weight, substantially entirely within the pores of a gamma-alumina or silica-alumina support having a surface area of greater than 50 $m^2/gm$ and a porosity greater than about 0.4 cc/gm. The vanadia was placed substantially entirely within the pores of the support, in molten form, by a fusion technique, as described more particularly in U.S. Pat. No. 3,925,447 which is hereby incorporated by reference.

The contacting of the alkyl substituted piperidine with ammonia is effected in the vapor phase in the presence of the supported vanadia catalyst, as hereinabove described, and in the substantial absence of free (molecular) oxygen, at temperatures from about 575° F to about 930° F, preferably from about 700° F to 850° F. Vanadia is in its oxidized form and provides oxygen to the process, and is itself reduced during the process. The reduced vanadia is periodically regenerated to its oxidized state by contact with molecular oxygen in a separate reaction zone.

The reaction effluent includes nicotinonitrile, as well as unreacted alkyl piperidine and alkyl pyridine reaction intermediate, with the nicotinonitrile being recovered as a product, and the unreacted alkyl piperidine and alkyl pyridine reaction intermediate being recycled to the reaction for ultimate conversion to nicotinonitrile.

The invention will be further described with respect to an embodiment thereof illustrated in the accompanying drawing, wherein:

The drawing is a simplified schematic flow diagram of an embodiment of the present invention.

Referring now to the drawing, an alkyl piperidine, such as 3-methyl piperidine in line 10 and ammonia in line 11 are introduced into a nicotinonitrile production reactor, schematically indicated as 12. The reactor 12 is preferably a fluidized reactor, although other types of reactors, such as a fixed bed reactor could also be employed; however, the fluidized reactor is preferred. In reactor 12 the ammonia and alkyl piperidine react in the absence of oxygen, and in the presence of an oxidized supported vanadia catalyst, of the type hereinabove described, introduced through line 13 to effect production of nicotinonitrile.

A reaction effluent, containing nicotinonitrile, as well as unreacted feed material, an alkyl pyridine reaction intermediate, is withdrawn from reactor 12 through line 14 and introduced into a separation and recovery zone, schematically indicated as 15. Nicotinonitrile reaction product recovered in zone 15 is withdrawn through line 16.

Unreacted alkyl piperidine, as well as alkyl pyridine reaction intermediate, recovered in zone 15 is recycled to reactor 12 through line 17.

Reduced supported vanadia catalyst is withdrawn from reactor 12 through line 18 and introduced into a stripping vessel, schematically indicated as 19, wherein the catalyst is contacted with an inert stripping gas, such as, steam, nitrogen and the like, introduced through line 21, for the purpose of stripping volatile matter from the supported vanadia catalyst.

Reduced supported vanadia catalyst, withdrawn from reactor 19 through line 22, is introduced into a catalyst regenerator, schematically indicated as 23, wherein the catalyst is contacted with molecular oxygen introduced through line 24 to effect regeneration of the supported vanadia by oxidation thereof to its oxidized valence state; namely, vanadium pentoxide. The oxidized supported vanadia is withdrawn from regenerator 23 through line 13 and introduced into the nicotinonitrile production reactor 12.

The invention will be further described with respect to the following example; however, the scope of the invention is not to be limited thereby.

EXAMPLE

In the following example, the catalyst was 40 wt% vanadia supported, by fusion, substantially entirely within the pores of a silica-alumina support having a surface area of greater than 50 $m^2/g$ and a porosity greater than 0.4 cc/g. (Grace-135). The experiment was conducted in a circulating fluid bed reactor system consisting of a reactor, stripper and regenerator, each 1 inch dia. × 4 feet and containing 400 g. of the catalyst. Feed to the reactor was 3-methyl piperidine and ammonia, feed to the regenerator was air and feed to the stripper was nitrogen. Operating conditions and results are shown in Table I.

TABLE I

| Operating Conditions | |
|---|---|
| Temperatures | |
| Reactor | 800° F |
| Stripper | 800° F |
| Regenerator | 900° F. |
| Pressure, atm. | 1 |
| Catalyst Circulation Rate, g/hr. | 3000 |
| Feed to Reactor, g. moles/hr. | |
| 3-methyl piperidine | 1.54 |
| Ammonia | 9.24 |
| Feed to Regenerator, g. moles/hr. | |
| Air | 14.0 |
| Conversion, mole % | 100 |
| Selectivities, mole % | |
| Nicotinonitrile | 14.7 |
| β-Picoline | 51.1 |
| Pyridine | 6.9 |
| Unknown | 6.5 |
| Carbon Oxides | 20.8 |
| Ultimate Yield to Nicotinonitrile[a] | 58.1 |

[a]Nicotinonitrile selectivity +0.85 (β-picoline selectivity).

Numerous modifications and variations of the present invention are possible in light of the above teachings and, therefore, within the scope of the appended claims, the invention may be practiced otherwise than as particularly described.

What is claimed is:

1. A process for producing a cyano-pyridine, comprising:
contacting an alkyl piperidine with ammonia in the absence of any gaseous oxygen and in the presence of oxidized vanadia supported on a porous support, said support containing from about 25% to about 75%, by weight, of the vanadia having been placed in molten form substantially entirely within the pores of the support, the support having a surface area greater than about 50 $m^2$/gm and a porosity greater than about 0.4 cc/gm, said support being selected from the group consisting of gamma-alumina and silica-alumina.

2. The process of claim 1 wherein the alkyl piperidine has at least one alkyl group, said at least one alkyl group being in the three position.

3. The process of claim 2 wherein the alkyl piperidine is selected from the group consisting of 3-methyl piperidine, 3-ethyl piperidine, 2,3-dimethyl piperidine, 2,5-dimethyl piperidine and 2-methyl-5-ethyl piperidine and the cyanopyridine is nicotinonitrile.

4. The process of claim 3 wherein the contacting is effected at a temperature of from about 575° F to about 930° F.

5. The process of claim 4 wherein the oxidized vanadia supported on a porous support is periodically regenerated with gaseous oxygen in a separate contacting step.

6. The process of claim 5 wherein the alkyl piperidine is 3-methyl piperidine.

* * * * *